(12) United States Patent
Xu et al.

(10) Patent No.: US 12,566,163 B2
(45) Date of Patent: Mar. 3, 2026

(54) APPARATUS FOR PERFORMING SENSOR CALIBRATIONS AND BUMP TESTS

(71) Applicant: Molex, LLC, Lisle, IL (US)

(72) Inventors: Miao Xu, Bolingbrook, IL (US);
Wenfeng Peng, North Aurora, IL (US);
Amram Netanel Afenzer, Skokie, IL (US); Brian Michael Zappa, Wood Dale, IL (US)

(73) Assignee: Molex, LLC, Lisle, IL (US)

( * ) Notice: Subject to any disclaimer, the term of this patent is extended or adjusted under 35 U.S.C. 154(b) by 312 days.

(21) Appl. No.: 18/570,089

(22) PCT Filed: Jul. 15, 2022

(86) PCT No.: PCT/IB2022/056543

§ 371 (c)(1),
(2) Date: Dec. 14, 2023

(87) PCT Pub. No.: WO2023/002322

PCT Pub. Date: Jan. 26, 2023

(65) Prior Publication Data

US 2024/0280552 A1      Aug. 22, 2024

Related U.S. Application Data

(60) Provisional application No. 63/223,091, filed on Jul. 19, 2021.

(51) Int. Cl.
*G01N 33/00* (2006.01)
(52) U.S. Cl.
CPC ....... *G01N 33/0006* (2013.01); *G01N 33/007* (2013.01)

(58) Field of Classification Search
None
See application file for complete search history.

(56) References Cited

U.S. PATENT DOCUMENTS

| | | | |
|---|---|---|---|
| 3,949,599 A | 4/1976 | Kruishoop | |
| 4,063,446 A | 12/1977 | Fuhrmann | |
| 5,214,952 A | 6/1993 | Leggett et al. | |

(Continued)

FOREIGN PATENT DOCUMENTS

| | | |
|---|---|---|
| CA | 3113159 A1 | 5/2021 |
| WO | 2020191482 A1 | 10/2020 |

OTHER PUBLICATIONS

International Preliminary Report on Patentability received for PCT Application No. PCT/IB2022/056543, mailed on Feb. 1, 2024, 5 pages.

(Continued)

*Primary Examiner* — Jonathan M Dunlap

(57) ABSTRACT

An apparatus performing sensor calibrations and bump tests includes a housing having first and second gas paths. The first gas path has a filter for filtering gas passing therethrough. A three-way valve may be provided between the inlet and the paths. A first valve may be provided between the inlet and the first path and a second valve may be provided between the inlet and the second path. Gas flows through the first path upon activation of the valve(s) to a first condition, and gas flows through the second path upon activation of the valve(s) to a second condition. A calibration cap is coupled to the outlet and to a sensor. A gas standard bottle is coupled to the inlet. A method of using same is also disclosed.

22 Claims, 4 Drawing Sheets

(56)  References Cited

U.S. PATENT DOCUMENTS

| | | |
|---|---|---|
| 6,200,819 B1 | 3/2001 | Harvey et al. |
| 2012/0125076 A1 | 5/2012 | Tryfonos |
| 2014/0091939 A1 | 4/2014 | Won |
| 2015/0185177 A1 | 7/2015 | Xie et al. |
| 2018/0267003 A1 | 9/2018 | Johnson |
| 2019/0219472 A1 | 7/2019 | Huang |

OTHER PUBLICATIONS

International Search Report and Written Opinion received for PCT
Application No. PCT/IB2022/056543, mailed on Nov. 1, 2022, 8
pages.

APPARATUS FOR PERFORMING SENSOR CALIBRATIONS AND BUMP TESTS

RELATED APPLICATIONS

This application is a U.S. National Phase Patent Application of International Patent Application No. PCT/IB2022/056543, filed on Jul. 15, 2022, which claims priority to U.S. Provisional Patent Application No. 63/223,091, filed Jul. 19, 2021, both of which are incorporated herein by reference in their entireties.

FIELD OF THE DISCLOSURE

This disclosure relates to an apparatus that is configured for improved operations when performing sensor calibrations and bump tests and the general operation of such an apparatus.

DESCRIPTION OF RELATED ART

The requirements of sustainable and environmentally friendly industrial production have drawn increased attention from the general public in recent years. Various sensor technologies have been employed to address those safety and environmental concerns. Due to the nature of the sensor working principle, one significant challenge of such a sensor-based system is that the sensitivities of the sensors utilized in the system will change (decrease) over time due, at least in part, to field conditions including weather, run-time, and environmental chemical exposures. As an example, in many areas of the world, heavy contaminations in the air can significantly accelerate the sensitivity decrease of sensors and harm the reliability of sensors. Accurate field calibration and bump tests are effective ways to address these challenges by providing precise sensitivity and confirmation of sensitivity.

Field calibrations include calibration checks and full calibrations. Calibration checks expose the sensor to a test gas to verify that the sensor and its alarm(s) respond within the manufacturer's acceptable limits. Full calibrations adjust sensor's response to match the desired value compared to a known concentration of gas. Bump tests, conversely, involve passing calibration gas over the sensor at a concentration above the alarm set points in order to trigger the alarm. Thus, unlike calibrations, bump tests do not measure the accuracy of the sensor, but rather are used to give confidence in the ability of the sensor to recognize and respond when a hazard is present.

The precision of the field calibrations and bump tests rely on the stable, trustworthy baseline and response. Because of the complexity of field conditions, e.g., contaminations, wind, and humidity variance, it is usually challenging to obtain a stable and trustworthy baseline for accurate field calibrations and bump tests. Apart from the gas standard bottle that field technicians already carry, they might need to carry another clean gas bottle and use this bottle to afford a clean and reliable baseline. However, the usage of another gas bottle will not only increase the time, labor, and material cost, but also raise safety concerns of carrying extra bottles to the field, especially when climbing high towers. There is a critical business need to providing a cost-efficient and reliable apparatus to tackle these difficulties when performing sensor calibrations and bump tests.

As a result of the foregoing, certain individuals would appreciate further improvements in such apparatuses and the operation of same.

BRIEF SUMMARY

Accordingly, in an embodiment, the present disclosure provides an apparatus configured for performing sensor calibrations and bump tests. The apparatus includes a housing having a gas inlet and a gas outlet, and first and second gas paths extending therebetween. The first gas path has a filter which filters the gas passing therethrough. In a first embodiment, a three-way valve is provided between the gas inlet and the gas paths. In a second embodiment, a first valve is provided between the gas inlet and the first gas path and a second valve is provided between the gas inlet an the second gas path. Gas flows through the first gas path upon activation of the valve(s) to a first condition, and gas flows through the second gas path upon activation of the valve(s) to a second condition. A calibration cap is coupled to the gas outlet and to a sensor. A gas standard bottle is coupled to the gas inlet.

In an embodiment, the present disclosure provides a method of operating an apparatus for performing sensor calibrations and bump tests. The method includes connecting a gas standard bottle to an apparatus: connecting a calibration cap of the apparatus to a sensor configured to sense properties of gas: turning the gas standard bottle on to allow gas to flow out of the gas standard bottle and into the apparatus: activating at least one valve of the apparatus to allow gas to flow along a first gas path through the apparatus to the calibration cap and to the sensor, wherein the first gas path includes an inline filter through which gas flows: commencing a calibration program of the sensor to perform a baseline collection: after completion of the baseline collection, activating the at least one valve to allow gas to flow along a second gas path through the apparatus to the calibration cap and to the sensor, wherein the second gas path does not have an inline filter through which gas flows: after a gas response collection performed by the sensor has been completed, disconnecting the calibration cap from the sensor; and ending the calibration program of the sensor.

BRIEF DESCRIPTION OF THE DRAWINGS

The present disclosure is illustrated by way of example, and not limited, in the accompanying figures in which like reference numerals indicate similar elements and in which.

DETAILED DESCRIPTION

Figure 1:
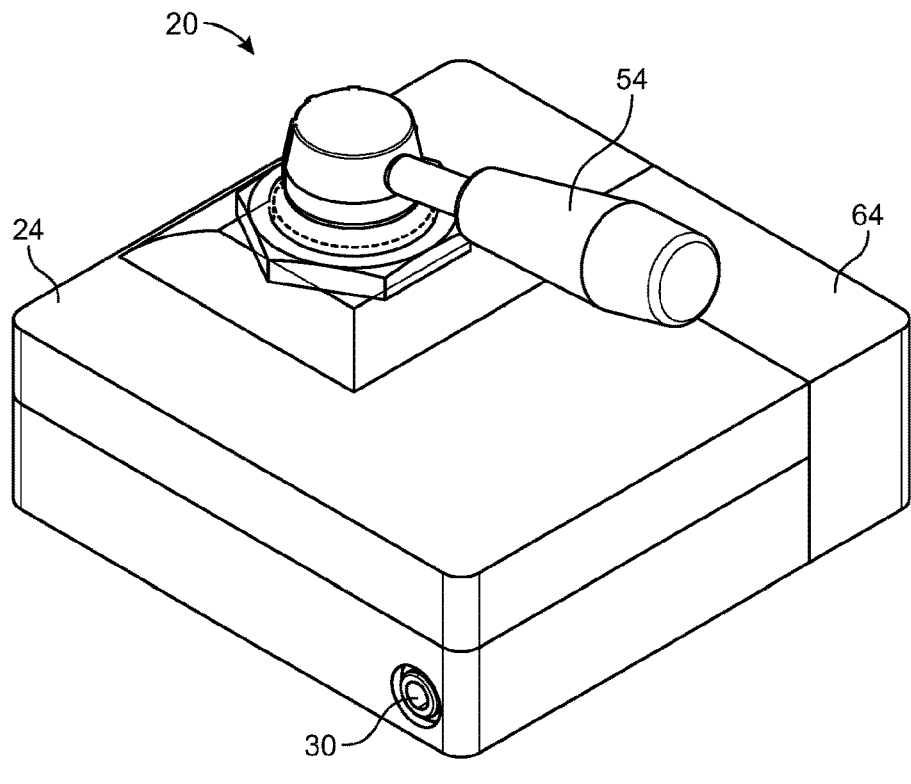
FIG. 1 depicts a perspective view of a first embodiment of an apparatus configured to perform sensor calibrations and bump tests of a sensor.

While the disclosure may be susceptible to embodiment in different forms, there is shown in the drawings, and herein will be described in detail, specific embodiments with the understanding that the present disclosure is to be considered an exemplification of the principles of the disclosure and is not intended to limit the disclosure to that as illustrated and described herein. Therefore, unless otherwise noted, features disclosed herein may be combined to form additional combinations that were not otherwise shown for purposes of brevity. It will be further appreciated that in some embodiments, one or more elements illustrated by way of example in a drawing(s) may be eliminated and/or substituted with alternative elements within the scope of the disclosure.

Figure 2:
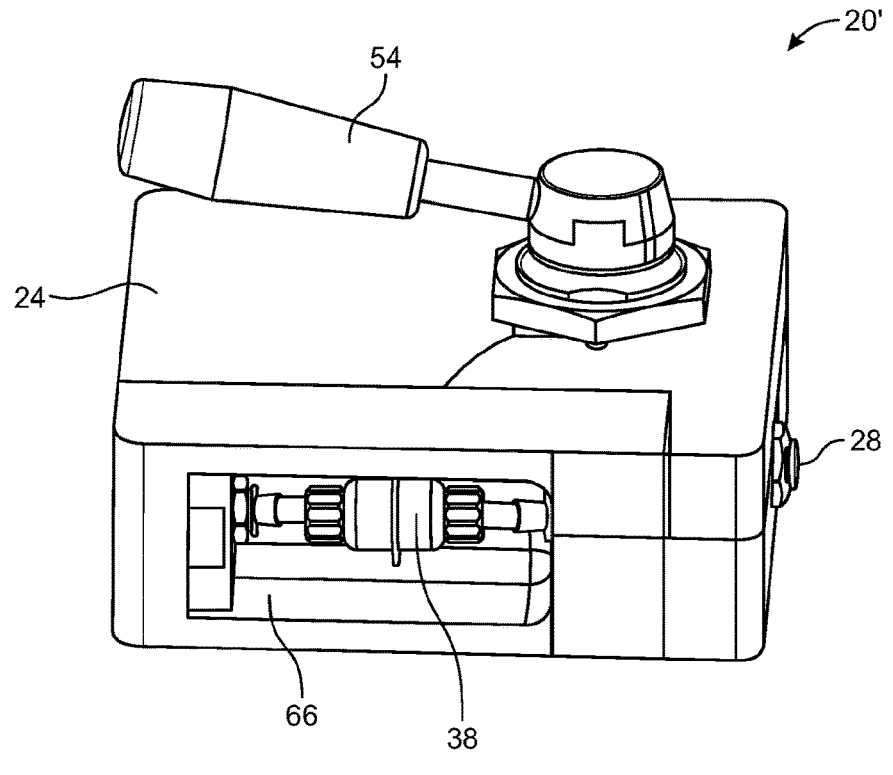
FIG. 2 depicts a perspective view of a second embodiment of an apparatus configured to perform sensor calibrations and bump tests of a sensor.
Figure 3:
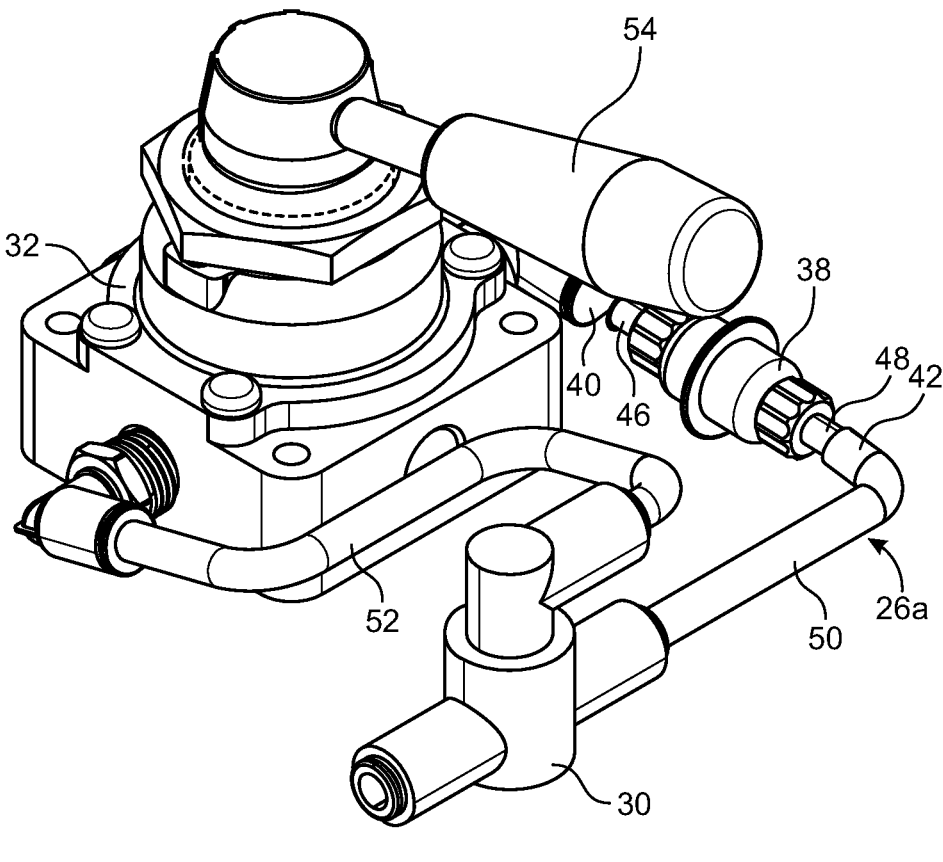
FIG. 3 depicts a perspective view of the apparatus with a housing removed to show internal components.

An apparatus 20, 20' is provided which is configured for improved operations when performing sensor calibrations and bump tests of a sensor 22 which is permanently coupled to a fixture or structure in a refinery, such as a gas pipe, for example. As shown in FIGS. 1 and 2, the apparatus 20, 20' includes a housing 24 having a fluid path arrangement 26a, 26b extending from a gas inlet 28 of the housing 24 and a gas outlet 30 of the housing 24. A representative drawing of a first embodiment of the fluid path arrangement 26a is provided in FIG. 4 and a representative drawing of a second embodiment of the fluid path arrangement 26b is provided in FIG. 5. The housing 24 may be formed of plastic.

Figure 4:
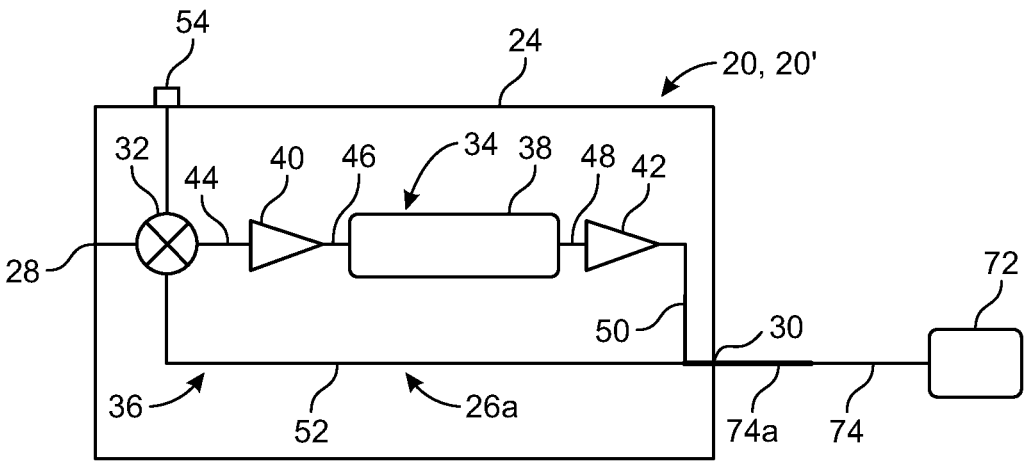
FIG. 4 depicts a schematic of a first embodiment of a fluid path provided in the apparatus.

Attention is invited to the first embodiment of the fluid path arrangement 26a shown in FIG. 4. The fluid path arrangement 26a includes a 3-way switch or valve 32 is mounted within the housing 24 and is coupled to the gas inlet 28. A first gas path 34 extends between the valve 32 and the gas outlet 30, and a second gas path 36 extends between the valve 32 and the gas outlet 30. The first gas path 34 includes a filter 38 through which the gas must flow, while the second gas path 36 does not include a filter 38. A check valve or valves may be provided in the first gas path 34 so that gas only flows in one direction along the first gas path 34. As shown in the illustrated embodiment, a first check valve 40 is provided in the gas path downstream of the valve 32 and upstream of the filter 38, and a second check valve 42 is provided in the gas path downstream of the filter 38 and upstream of the gas outlet 30. The gas outlet 30 may be provided by a check valve. The first and second check valves 40, 42 are not required. The filter 38 may include any appropriate filtration material, such as, but not limited to, active carbon or precious metals.

In the embodiment as shown, a first path portion 44 is connected at a first end thereof to the 3-way valve 32 and at a second end thereof to the first check valve 40. A second path portion 46 is connected at a first end thereof to the first check valve 40 and at a second end thereof to the filter 38. If the first check valve 40 is not provided, then only a single path portion is provided between the 3-way valve 32 and the filter 38. A third path portion 48 is connected at a first end thereof to the filter 38 and at a second end thereof to the second check valve 42. A fourth path portion 50 is connected at a first end thereof to the second check valve 42 and at a second end thereof to the gas outlet 30. If the second check valve 42 is not provided, then only a single path portion is provided between the filter 38 and the gas outlet 30. The path portions 44, 46, 48, 50 may be provided by tubing, or may be molded into the housing 24. The connections between the components are sealed by suitable means to prevent gas from leaking out of the first gas path 34. The second gas path 36 is formed by a path 52 connected at a first end thereof to the 3-way valve 32 and at a second end thereof to the gas outlet 30. The path 52 may be provided by tubing, or may be molded into the housing 24. The components used to form the second gas path 36 are sealed to prevent gas from leaking out of the second gas path 36. The 3-way valve 32 is actuated by a handle 54 which extends from the housing 24 and can be grasped by a user.

Figure 5:
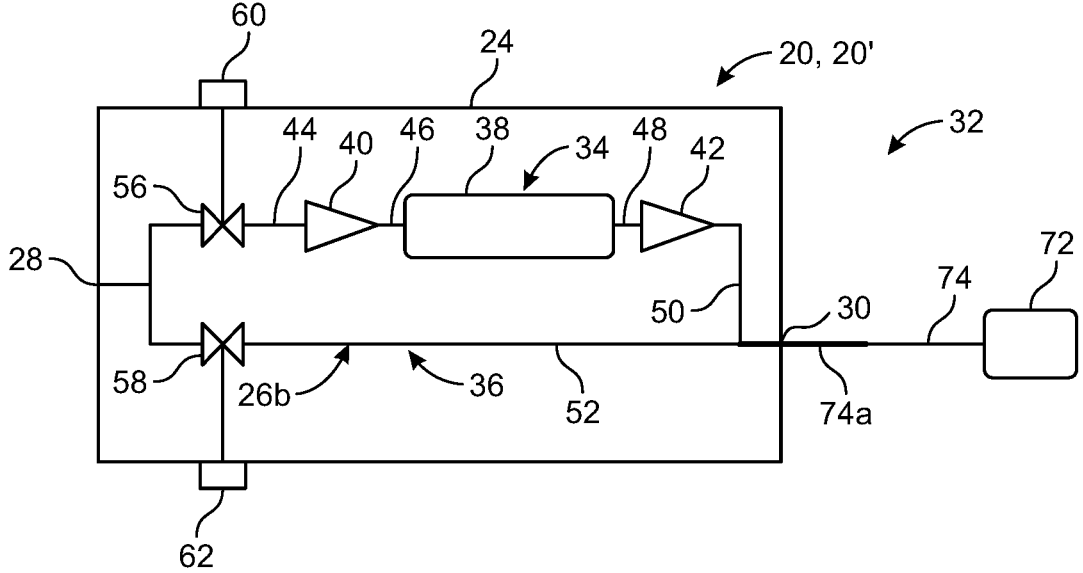
FIG. 5 depicts a schematic of a second embodiment of a fluid path provided in the apparatus.

Attention is invited to the second embodiment of the fluid path arrangement 26b shown in FIG. 5. The second embodiment of the fluid path arrangement 26b is identical to the first embodiment of the fluid path arrangement 26b except for the differences noted herein.

The 3-way switch or valve 32 of the first embodiment is replaced by a first valve 56 mounted within the housing 24 and which is coupled between the gas inlet 28 and the first path portion 44 of the first gas path 34, and a second valve 58 mounted within the housing 24 and which is coupled between the gas inlet 28 and the path 52 of the second gas path 36. Each valve 56, 58 can be operated by a handle 60, 62 which extends from the housing 24 and can be grasped by a user. The first valve 56 is coupled to the first path portion 44, and the second valve 58 is coupled to the path 52. The connections between the first valve 56 and the first path portion 44 and the second valve 58 and the path 52 are sealed by suitable means to prevent gas from leaking out of the gas paths 34, 36.

As shown in FIG. 1, the housing 24 of the apparatus 20 includes a removable cover 64 which covers the filter 38. When the cover 64 is removed, the filter 38 can be withdrawn from the housing 24, replaced and reinserted. Suitable quick connections can be provided to easily and quickly detach and reattach the filter 38 to the fluid arrangement 26a, 26b, while maintaining the fluid seal with the remainder of the fluid arrangement 26a, 26b to ensure that gas leakage from the housing 24 is prevented. Thereafter, the cover 64 is reattached to the remainder of the housing 24. Suitable seals between the cover 64 and the remainder of the housing 24 can be provided to ensure that gas leakage from the housing 24 is prevented. Because the filter 38 can be replaced, this prolongs the life of the apparatus 20.

As shown in FIG. 2, the housing 24 of the apparatus 20' includes a cavity 66 in which the filter 38 is positioned. Suitable quick connections can be provided to easily and quickly detach and reattach the filter 38 to the fluid arrangement 26a, 26b, while maintaining the fluid seal with the remainder of the fluid arrangement 26a, 26b to ensure that gas leakage from the housing 24 is prevented. The filter 38 can be withdrawn from the cavity 66, replaced and reinserted. Because the filter 38 can be replaced, this prolongs the life of the apparatus 20'.

Figure 6:
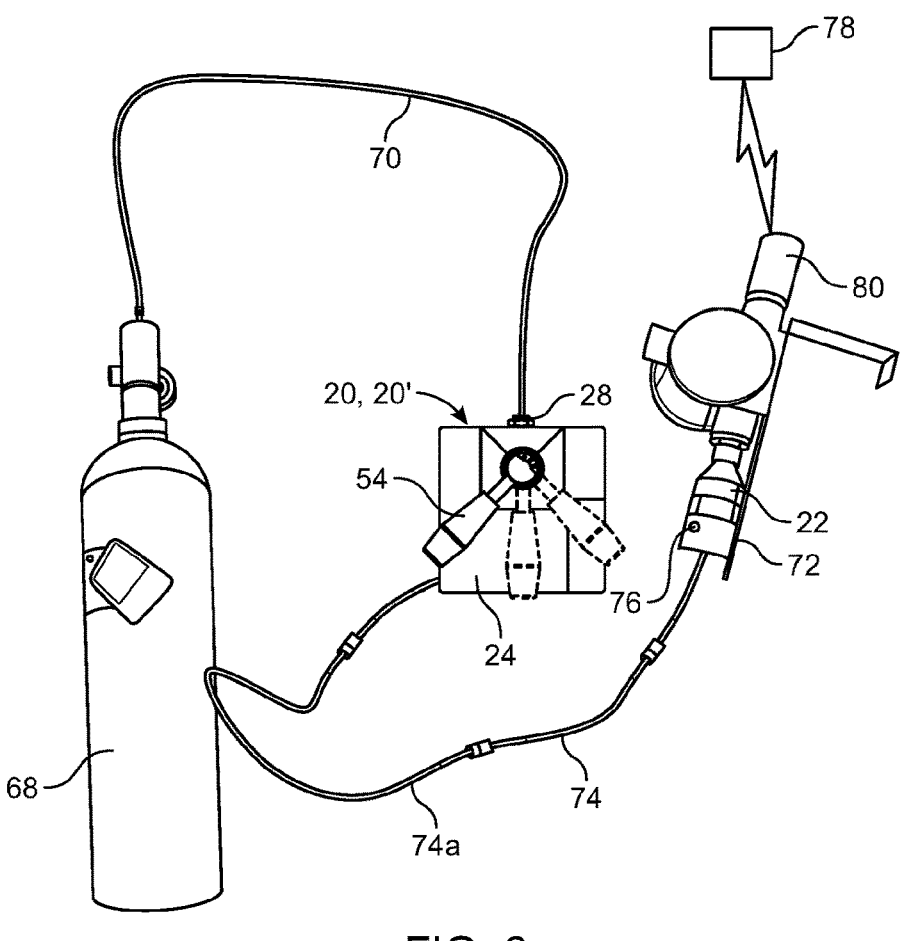
FIG. 6 depicts a top plan view of a system which includes the apparatus, a gas standard bottle, a sensor, a transmitter and a control system.

As shown in FIG. 6, a gas standard bottle 68 is connected to the gas inlet 28, and may be coupled to the gas inlet 28 by tubing 70. As shown, the tubing 70 is connected at a first end thereof to the gas standard bottle 68 and is connected at a second end thereof to the gas inlet 28.

A calibration cap 72 is coupled to the gas outlet 30 of the apparatus 20, 20' by tubing 74. A first end of the tubing 74 is coupled to the gas outlet 30 and a second end of the tubing 74 is coupled to the calibration cap 72. In some embodiments, the tubing 74 can include a humidity compensation fixture 74a which may be formed of any appropriate material, such as, for example, NAFION tubing (NAFION is a trademark of The Chemours Company FC, LLC). The calibration cap 72 forms a chamber in which the sensor 22 is inserted. The chamber allows for gas being tested by the sensor 22 to accumulate therein to ensure that an adequate concentration of the gas is being tested. Therefore, gas concentration in the chamber of the calibration cap 72 is the same as, or approximately the same as, the gas concentration in the gas standard bottle 68. This provides for greater accuracy. In an embodiment, the calibration cap 72 has a magnet 76 that magnetically attaches to the sensor 22 to provide for a quick connect and which allows for the easy release of the calibration cap 72 from the sensor 22. The tubing 74 coupling the calibration cap 72 to the gas outlet 30 may be flexible. This allows the user to snake the calibration cap 72 into spaces which are not easily accessible.

The sensor 22 is operatively coupled to a control system 78 which receives information from the sensor 22 and determines properties of the gas being sensed by the sensor 22. The sensor 22 may be coupled to a transmitter 80 which is, in turn, in communication with the control system 78. The control system 78 may be a tablet or a smart phone with a mobile application installed for performing sensor calibrations, bump tests, and other sensor related activities such as device onboarding, troubleshooting and post-detection investigations.

In the embodiment shown in FIGS. 1-4, the handle 54 is rotatably mounted on the housing 24. Upon rotation of the handle 54, the valve 32 can be placed in a first condition in which gas can flow through the valve 32 and into the first gas path 34, but cannot flow through the valve 32 and into the second gas path 36, and the valve 32 can be placed in a second condition in which gas cannot flow through the valve 32 and into the first gas path 34, but can flow through the valve 32 and into the second gas path 36. Thus, the valve 32 is used to select whether the gas will flow along the first gas path 34 or the second gas path 36, and the valve 32 can be adjusted as desired depending on the operation being performed. In an embodiment, the valve 32 can be placed in a third condition in which gas cannot flow through the valve 32 and into the first gas path 34 or into the second gas path 36. The check valve or valves 40, 42, if provided, prevent gas backflow along the first gas path 34. In an embodiment, the check valve 40, 42 or check valves 40, 42 are eliminated. The filter 38 filters analyte from the gas in the gas standard bottle 68 to afford a "clean" carrier gas. If the humidity compensation fixture 74a is provided, the humidity compensation fixture 74a minimizes the humidity difference between zero air and environment air in order to create a smooth baseline.

A method of operating the apparatus 20, 20' which has the fluid arrangement 26a of FIG. 4 is now described. In a first step, the gas standard bottle 68 is connected to the gas inlet 28 of the apparatus 20, 20'. In a second step, the gas standard bottle 68 is turned on, the valve 32 is actuated to be placed into the first condition to allow gas to flow through the valve 32 and along the first gas path 34, and the calibration cap 72 is connected to the sensor 22. In a third step, the control system 78 runs a calibration program of the sensor 22 using information collected by the sensor 22 regarding properties of the gas in the chamber of the calibration cap 72, and a user waits for the completion of the baseline collection. In a fourth step, once the baseline collection is finished, the valve 32 is actuated to be placed into the second condition to allow gas to flow through the valve 32 and along the second gas path 36, the control system 78 runs a gas response collection using information collected by the sensor 22 regarding properties of the gas in the chamber of the calibration cap 72, and the user waits for the finish of the gas response collection by the sensor 22. In a fifth step, the calibration cap 72 is disconnected from the sensor 22, the gas bottle 68 is turned off, and the calibration program is deactivated. In this fifth step, the valve 32 may be actuated to be placed into the third condition.

In areas with a relatively clean background, the baseline collection by the sensor 22 can be collected with the environment air, and the gas response collection can be collected only with the second gas path 36. In such an instance, an alternative method of operating the apparatus 20, 20' is described. In a first step, the operator confirms that the background is clean, the calibration program of the sensor 22 is started and a user waits for the completion of the baseline collection. In a second step, the gas standard bottle 68 is turned on, the valve 32 is actuated to be placed into the second condition to allow gas to flow along the second gas path 36, the calibration cap 72 is connected to the sensor 22, and the user waits for the completion of the gas response collection. In a third step, the calibration cap 72 is disconnected from the sensor 22, the gas bottle 68 is turned off, and the calibration program is deactivated. In this third step, the valve 32 may be actuated to be placed into the third condition.

In the embodiment shown in FIG. 5, the handles 60, 62 are rotatably mounted on the housing 24. Upon rotation of the handles 60, 62 into a first condition, the valve 56 allows gas to flow therethrough and into the first gas path 34 and the valve 58 prevents gas to flow therethrough and into the second gas path 36. Upon rotation of the handles 60, 62 into a second condition, the valve 56 prevents gas to flow therethrough and into the first gas path 34 and the valve 58 allows gas to flow therethrough and into the second gas path 36. Thus, the valves 56, 58 are used to select whether the gas will flow along the first gas path 34 or the second gas path 36, and the valves 56, 58 can be adjusted as desired depending on the operation being performed. In an embodiment, the valves 56, 58 can be placed in a third condition in which gas cannot flow through the valve 56 and into the first gas path 34 and gas cannot flow through the valve 58 and into the second gas path 36. The check valve or valves 40, 42, if provided, prevent gas backflow along the first gas path 34. In an embodiment, the check valve 40, 42 or check valves 40, 42 are eliminated. The filter 38 filters analyte from the gas in the gas standard bottle 68 to afford a "clean" carrier gas. If the humidity compensation fixture 74a is provided, the humidity compensation fixture 74a minimizes the humidity difference between zero air and environment air in order to create a smooth baseline.

A method of operating the apparatus 20, 20' which has the fluid arrangement 26b of FIG. 5 is now described. In a first step, the gas standard bottle 68 is connected to the gas inlet 28 of the apparatus 20, 20'. In a second step, the gas standard bottle 68 is turned on, the first valve 56 is actuated to be opened to allow gas to flow from the gas inlet 28, through the first valve 56, along the first gas path 34 to the gas outlet 30, and the second valve 58 is actuated to be closed to prevent the flow of gas through the second valve 58 and into the second gas path 36, and the calibration cap 72 is connected to the sensor 22. When the first valve 56 is open and the second valve 58 is closed, this defines the first condition. In a third step, a calibration program of the sensor 22 is started and an operator waits for the finish of the baseline collection by the sensor 22. In a fourth step, once the baseline collection is finished, the first valve 56 is actuated to be closed to prevent the flow of gas through the first valve 56 and into the first gas path 34, and the second valve 58 is actuated to be opened to allow gas to flow from the gas inlet 28, through the second valve 58, along the second gas path 36 to the gas outlet 30, and the user waits for the finish of a gas response collection by the sensor 22. When the first valve 56 is closed and the second valve 58 is open, this defines the second condition. In a fifth step, the calibration cap 72 is disconnected from the sensor 22, each valve 56, 58 is actuated to be closed, the gas bottle 68 is turned off, and the calibration program of the sensor 22 is deactivated. When the first and second valves 56, 58 are closed, this defines a third condition.

In areas with a relatively clean background, the baseline collection by the sensor 22 can be collected with the environment air, and the gas response collection can be collected only with the second gas path 36. In such an instance, an alternative method of operating the apparatus 20, 20' is described. In a first step, the operator confirms that the background is clean, the calibration program of the sensor 22 is started and a user waits for the finish of the baseline collection. In a second step, the gas standard bottle 68 is turned on, the first valve 56 is actuated to be closed, the second valve 58 is actuated to be opened to allow gas to flow through the second valve 58 and along the second gas path 36, the calibration cap 72 is connected to the sensor 22, and the user waits for the finish of the gas response collection. In a third step, the calibration cap 72 is disconnected from the sensor 22, the second valve 58 is closed, the gas bottle 68 is turned off, and the calibration program of the sensor 22 is deactivated.

Figure 7:
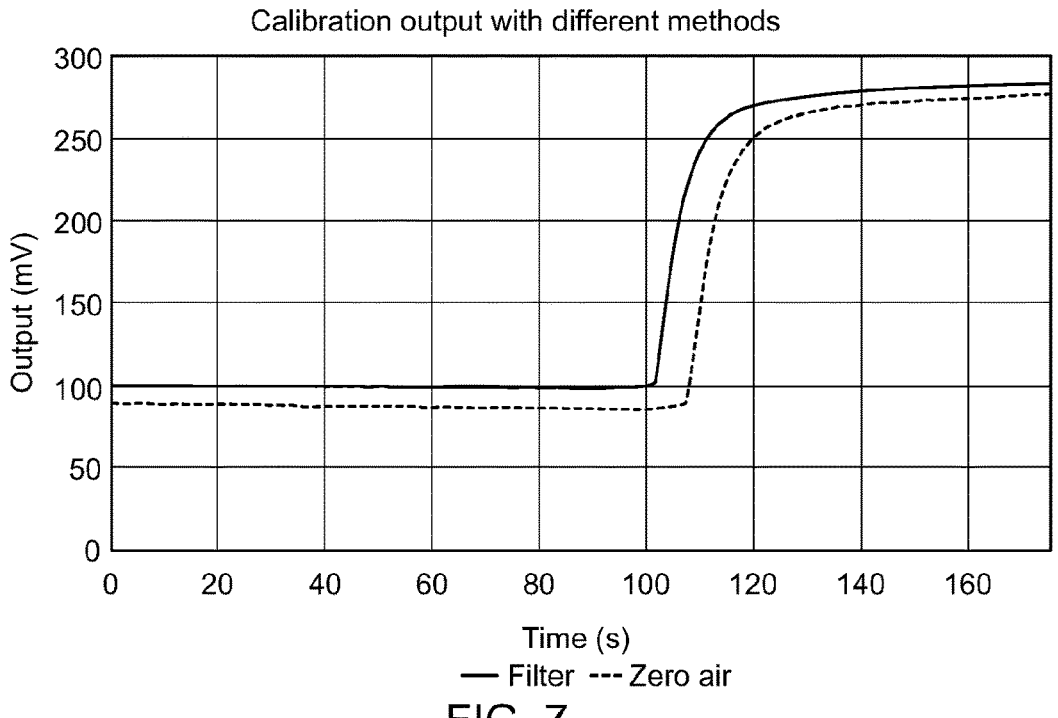
FIG. 7 depicts a graph showing calibration output.

The calibration result with the proposed methods is close to the result with zero air. As illustrated in the graph of FIG. 7, delta output after gas exposure with the filter 38 is approximately 97% of delta output with zero air. The apparatus 20, 20' in use with the gas standard bottle 68 and the sensor 22, collectively a system, thus provides a benefit over prior art apparatuses/systems. More specifically, the apparatus 20, 20' not only reduces the equipment required for a calibration (a second clean gas bottle is not required), but also maintains the accuracy of the calibration test.

The inclusion of the humidity compensation fixture 74a as a part of the apparatus 20, 20' is ideally suited to be used in locations/environments where the operation/accuracy of sensors 22 may be affected by humidity. However, in an alternative, if the apparatus 20, 20 is intended to be used in locations/environments where the operation/accuracy of sensors 22 would likely not be affected by humidity (e.g., in dry locations/environments, such as a desert), the apparatus 20, 20' does not include humidity compensation fixture 74a. Operation of this alternative embodiment of the apparatus 20, 20' would be identical to operation of first embodiment of the apparatus 20, 20' as described herein.

While particular embodiments are illustrated and described with respect to the drawings, it is envisioned that those skilled in the art may devise various modifications without departing from the spirit and scope of the appended claims. It will therefore be appreciated that the scope of the disclosure and the appended claims is not limited to the specific embodiments illustrated in and discussed with respect to the drawings and that modifications and other embodiments are intended to be included within the scope of the disclosure and the appended drawings. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure and the appended claims. Further, the foregoing descriptions describe methods that recite the performance of a number of steps. Unless stated to the contrary, one or more steps within a method may not be required, one or more steps may be performed in a different order than as described, and one or more steps may be formed substantially contemporaneously. Finally, the drawings are not necessarily drawn to scale.

The disclosure provided herein describes features in terms of preferred and exemplary embodiments thereof. Numerous other embodiments, modifications and variations within the scope and spirit of the appended claims will occur to persons of ordinary skill in the art from a review of this disclosure.

We claim:

1. An apparatus configured for performing sensor calibrations and bump tests comprising:
   a housing having a gas inlet and a gas outlet, wherein a first gas path is defined between the gas inlet and the gas outlet through the housing, and a second gas path is defined between the gas inlet and the gas outlet through the housing, wherein a filter is provided along the first gas path to filter gas passing therethrough, at least one valve provided between the gas paths and the gas inlet, wherein gas flows through the first gas path upon activation of the at least one valve to a first condition, and wherein gas flows through the second gas path upon activation of the at least one valve to a second condition;
   tubing coupled to the gas outlet; and
   a calibration cap configured to be coupled to the tubing and to a sensor.

2. The apparatus of claim 1, further comprising a gas standard bottle coupled to the gas inlet.

3. The apparatus of claim 1, wherein the tubing is flexible.

4. The apparatus of claim 1, wherein the housing has a removable cover over the filter.

5. The apparatus of claim 1, wherein the at least one valve is a three-way valve coupled to the gas inlet, the first gas path and the second gas path.

6. The apparatus of claim 1, wherein the at least one valve is a first valve coupled to the gas inlet and the first gas path, and a second valve coupled to the gas inlet and to the second gas path.

7. The apparatus of claim 1, further comprising a humidity compensation fixture coupled to the gas outlet of the housing.

8. The apparatus of claim 7, wherein the humidity compensation fixture is humidity compensation tubing.

9. The apparatus of claim 1, wherein the first gas path further comprises at least one check valve which allows gas to flow through the first gas path in one direction.

10. The apparatus of claim 1, wherein the first gas path further comprises a first check valve upstream of the filter and a second check valve downstream of the filter, the check valves allowing gas to flow through the first gas path in one direction.

11. A system configured for performing sensor calibrations and bump tests comprising:
   a sensor configured to measure properties of a gas:
   a housing having a gas inlet and a gas outlet, wherein a first gas path is defined between the gas inlet and the gas outlet through the housing, and a second gas path is defined between the gas inlet and the gas outlet through the housing, wherein a filter is provided along the first gas path to filter the gas passing therethrough, at least one valve provided between the gas paths and the gas inlet, wherein gas flows through the first gas path upon activation of the at least one valve to a first condition, and wherein gas flows through the second gas path upon activation of the at least one valve to a second condition:
   tubing coupled to the gas outlet:
   a calibration cap coupled to the tubing and to the sensor; and
   a gas standard bottle coupled to the gas inlet.

12. The system of claim 11, wherein the tubing is flexible.

13. The system of claim 11, wherein the housing has a removable cover over the filter.

14. The system of claim 11, wherein the at least one valve is a three-way valve, the three-way valve being coupled to the gas inlet, the first gas path and the second gas path.

15. The system of claim 11, wherein the at least one valve is a first valve coupled to the gas inlet and the first gas path, and a second valve coupled to the gas inlet and to the second gas path.

16. The system of claim 11, further comprising a humidity compensation fixture coupled to the gas outlet of the housing.

17. The system of claim 16, wherein the humidity compensation fixture is humidity compensation tubing.

18. The system of claim 11, wherein the first gas path further comprises at least one check valve which allows gas to flow through the first gas path in one direction.

19. The system of claim 11, wherein the first gas path further comprises a first check valve upstream of the filter and a second check valve downstream of the filter, the check valves allowing gas to flow through the first gas path in one direction.

20. A method of operating an apparatus for performing sensor calibrations and bump tests comprising:

connecting a gas standard bottle to an apparatus:

connecting a calibration cap of the apparatus to a sensor configured to sense properties of gas:

turning the gas standard bottle on to allow gas to flow out of the gas standard bottle and into the apparatus:

activating at least one valve of the apparatus to allow gas to flow along a first gas path through the apparatus to the calibration cap and to the sensor, wherein the first gas path includes an inline filter through which gas flows:

commencing a calibration program of the sensor to perform a baseline collection:

after completion of the baseline collection, activating the at least one valve to allow gas to flow along a second gas path through the apparatus to the calibration cap and to the sensor, wherein the second gas path does not have an inline filter through which gas flows;

after a gas response collection performed by the sensor has been completed, disconnecting the calibration cap from the sensor; and ending the calibration program of the sensor.

21. The method of claim 20, wherein the at least one valve is a three-way valve coupled to a gas inlet, the first gas path and the second gas path, and wherein activating the valve to allow gas to flow along the first gas path comprises causing the valve to be moved to a first condition, and wherein activating the valve to allow gas to flow along the second gas path comprises causing the valve to be moved to a second, different condition.

22. The method of claim 20, wherein the at least one valve is a first valve coupled to a gas inlet and the first gas path and a second valve coupled to the gas inlet and to the second gas path, and wherein activating the valve to allow gas to flow along the first gas path comprises causing the first valve to be opened and the second valve to be closed, and wherein activating the valve to allow gas to flow along the second gas path comprises causing the first valve to be closed and the second valve to be opened.

\* \* \* \* \*